United States Patent
Peng et al.

(10) Patent No.: US 11,180,445 B2
(45) Date of Patent: Nov. 23, 2021

(54) METHOD FOR RECYCLING UREA IN UREA ADDUCT PROCESS

(71) Applicant: Zhejiang Medicine Co., Ltd. Xinchang Pharmaceutical Factory, Donglu (CN)

(72) Inventors: Yongjian Peng, Donglu (CN); Xinde Xu, Donglu (CN); Jinping Ma, Donglu (CN); Yanwen Zhang, Donglu (CN); Bin Shao, Donglu (CN)

(73) Assignee: Zhejang Medicine Co., Ltd Xinchang Pharmaceutical Factory, Donglu (CN)

( * ) Notice: Subject to any disclaimer, the term of this patent is extended or adjusted under 35 U.S.C. 154(b) by 0 days.

(21) Appl. No.: 15/519,552

(22) PCT Filed: Oct. 12, 2015

(86) PCT No.: PCT/CN2015/000685
§ 371 (c)(1),
(2) Date: Apr. 16, 2017

(87) PCT Pub. No.: WO2016/058282
PCT Pub. Date: Apr. 21, 2016

(65) Prior Publication Data
US 2017/0240507 A1    Aug. 24, 2017

(30) Foreign Application Priority Data

Oct. 17, 2014  (CN) .......................... 201410554974.4

(51) Int. Cl.
| | |
|---|---|
| *C07C 273/16* | (2006.01) |
| *C07C 7/152* | (2006.01) |
| *C11C 3/00* | (2006.01) |
| *C07C 57/12* | (2006.01) |
| *C07C 7/14* | (2006.01) |
| *C07C 51/43* | (2006.01) |
| *C07C 51/487* | (2006.01) |

(52) U.S. Cl.
CPC .............. *C07C 273/16* (2013.01); *C07C 7/14* (2013.01); *C07C 7/152* (2013.01); *C07C 51/43* (2013.01); *C07C 51/487* (2013.01); *C07C 57/12* (2013.01); *C11C 3/00* (2013.01); *Y02P 20/582* (2015.11)

(58) Field of Classification Search
CPC ........... C11B 3/02; C11B 7/0083; C07C 7/14; C07C 67/48; C07C 67/60; C07C 273/16; C07C 51/43; C07C 51/487; C07C 7/152
See application file for complete search history.

(56) References Cited

U.S. PATENT DOCUMENTS

| | | | | |
|---|---|---|---|---|
| 2,892,870 A | * | 6/1959 | Matile .................. | B01D 9/0018 564/73 |
| 5,847,209 A | * | 12/1998 | Gupta .................. | C07C 273/16 564/73 |
| 6,528,669 B1 | * | 3/2003 | Kulås ..................... | C07C 67/56 554/184 |
| 2002/0026063 A1 | * | 2/2002 | Luthria ................... | C11B 1/025 554/174 |
| 2016/0024423 A1 | * | 1/2016 | Wang ..................... | C11B 3/006 554/154 |

FOREIGN PATENT DOCUMENTS

| | | | | |
|---|---|---|---|---|
| CN | 102746947 | * | 10/2012 | ............. C07C 51/02 |
| CN | 103483305 A | * | 1/2014 | ............... C07C 7/14 |
| WO | WO 2014/140864 | * | 9/2014 | |

OTHER PUBLICATIONS

Williams, R. J. E., Investigations of crystal modification of urea, Explosives Research and Development Establishment, 13/M/67, Produced by the Clearing house for Federal Scientific & Technical information, 20 pages (Year: 1968).*
CN103483305 A, Pan Jian et al., Method for gathering/recovering VE (Vitamins E), squalene and polyunsaturated fatty acids from deodorized distillate of plant oil, English translation, 1 page abstract (Year: 2014).*
CN102746947 A, Hexi Zhang et al., Method for separating and purifying DHA (docosahexaenoic acid) and saturated fatty acid from schizochytrium limacinum oil, English translation, 14 pages (Year: 2012).*

* cited by examiner

Primary Examiner — Yate' K Cutliff
(74) Attorney, Agent, or Firm — Christopher Casieri

(57) ABSTRACT

The present invention discloses a method for recycling urea in the process of separating and purifying unsaturated substances through a urea adduction method. The method comprises the following steps: liposoluble substances containing target unsaturated components are used as raw materials, and subjected to urea adduction, crystallization and filtration to produce a filtrate, from which the specific unsaturated components are obtained; the urea adduct is dissolved in a polar solvent, and after the adducted adducts are layered and released, adding a certain solvent to the urea solution to adjust the polarity, then cooling for crystallization, and recycling the urea. The method can realize complete release of the adducted components and recycling and reuse of urea, and the process is simple, the recovery rate is high, and the adduction effect is not influenced when recycling urea for reuse, and the production cost of the urea adduct is reduced, thus alleviating the adverse impact of urea discharges on the environment.

16 Claims, No Drawings

METHOD FOR RECYCLING UREA IN UREA ADDUCT PROCESS

FIELD OF THE INVENTION

The present invention relates to a method for recycling urea and especially relates to a method for recycling and reusing urea in the process of separating and purifying unsaturated substances through a urea adduction method.

BACKGROUND OF THE INVENTION

There are many liposoluble substances containing unsaturated double bonds in molecular structure, such as VE, squalene, polyunsaturated fatty acids, linoleic acid, linolenic acid, DHA, EPA. These liposoluble substances widely exist in vegetable oils and animal oils, and have physiological activities such as oxidation resistance, anti-aging, improving immunity, reducing blood fat, and anticancer. Some components are necessary for human beings. Chronically lacking these components could cause cardiovascular disorder, low immunity, virus infection and other diseases. Therefore, they are widely used in foods, health care products and medicines. It would be necessary to separate and purify these substances in order to make these non biological activity substances application for foods, health care products and medicines, because these components rich in double bonds generally exist in a mixed form with other non biological activity substances.

A variety of methods have been applied for separating components with different saturation degree, such as rectification, cryogenic crystallization, solvent extraction, conventional adsorption chromatography, supercritical extraction. But there are some disadvantages such as insufficient separation, small handling capacity, high cost, difficult to industrialization, destruction of fatty acid structure. It would be difficult to be used for main purification methods in industrial production.

The urea adduction method is a conventional separation method. Urea molecules can be in linear compound axis and circles around the axis through a strong hydrogen bond, and can be tightly wrapped with long-chain organic compounds to form adducts. It would be easy for saturated and monounsaturated compounds to form adducts with urea molecules due to less double bonds of saturated and monounsaturated compounds. It would not be easy for polyunsaturated substances to be clathrated by urea because polyunsaturated substances have more double bonds of and carbon chain bending has a certain spatial configuration. Therefore it could achieve a separation between components with different saturation degree by crystallization and filtration after mixing urea molecules and samples. At present, the urea adduction method is widely used in the field of separation and purification of unsaturated fatty acids, and has a certain application for separation of liposoluble substances such as VE and squalene.

Jianxia Guo et al. separate and purify linoleic acids of safflower seed oils through a urea adduction method to obtain linoleic acid products having a content of more than 70%. Tsumg-Shi Yang et al. separate and purify linoleic acids from soybean oils through a urea adduction method to obtain linoleic acids having a purity of 82%. Yuan Chengling et al. enrich arachidonic acid (AA) of microbial oils through an urea adduction method to increase the concentration of AA from 38.29% to 78.97%.

US Patent Publication No. 2003/0027865 discloses a process of purification of unsaturated fatty acids in vegetable oil and fish oil through an urea adduction method. The content of linoleic of vegetable oils and the content of EPA of fish oil have been greatly improved after purification. A method for separating saturated and unsaturated fatty acids from algae oil is described in CN201210247842.8. The content of both DHA and DPA is more than 93% after adduction. The present patent also mentioned a method of recycling urea by water-soluble crystallization, but the recovery of urea would be lower, because of larger solubility of urea in water, lower crystallization temperature required and greater energy consumption.

Chinese Patent No. CN201310442757.1 relates to a method of enrichment of VE (Vitamins E), squalene and polyunsaturated fatty acids in deodorized distillates from vegetable oils, in particular, VE, squalene and polyunsaturated fatty acids with higher concentration are obtained by using the principle of the urea adduction, and the recovery is more than 80%.

Overall, it has been disclosed that some adducted separated objects by purification of unsaturated substances of an urea adduction method are mainly some double bond-rich fat-soluble substances comprising VE, polyunsaturated fatty acids, squalene, solanesol and so on. These processes have many advantages such as simple operation, easy to industrial production and so on.

Urea adductions also have some disadvantages of having a large amount of urea. Usage amount of urea is generally 1 to 10 times as much as the mass of an adducted object mass in the process of the urea adduction. Actual industrial production needs a large amount of urea. A large-scale use of urea would inevitably lead to an increase of total cost despite lower price of urea. Besides urea emissions would cause a greater impact on water and soil quality and consequently cause waste of resources.

At present, it has been reported that urea adducts almost in urea adduct processes have not been taken special treatment measures, urea is dissolved in water by stirring to release adducted substances in some patents. The purpose is mainly to obtain adducted substances with higher saturation. But no research is mentioned of the conditions and effects of urea recovery. In particular, the urea dissolved in water requires a lower temperature to achieve crystallization because of greater solubility of urea in water. So it would lead to high energy consumption and low recovery rate.

Furthermore, recycling urea with water as the solvent needs accompanying by a concentration step. On the one hand, the process is complicated, on the other hand, some impurity components have been enriched in the concentration, and consequently it would lead to lower purity of recovered urea, poor crystal form, and thereby affect adduct effects on reusing.

In order to solve the above problems, it would be very necessary to introduce a recycling step of urea in the urea adduct process. After the separation of unsaturated materials, it would be important for application of urea adduct technology in practical production to develop a simple and easy method of recycling urea and realize complete release of adducted saturated substances and full rapid crystallization of urea for reuse.

SUMMARY OF THE INVENTION

The present invention intends to reprocess urea adducts crystallized in the process of urea adductions, comprising adding a polar solvent in a certain proportion to realize dissolving and layering by adjusting an amount of solvent and solvent polarity. Then the adducted substances are released from the upper layer. Adding a certain amount of solvent to the lower solution adjusts a polarity, and urea crystals can be crystallized under certain conditions, and then recycle and reuse urea after treatment. All of the used reagents can achieve reuse. Thereby it could decrease production costs and reduce adverse impacts on the environment.

In view of the above problems, the purpose of the present invention is to provide a method of recycling and reusing urea in the process of purifying unsaturated substances by a urea adduct method.

The present invention is to provide a method of recycling urea in the process of purifying unsaturated substances through a urea adduction method to accomplish the purpose of the present invention. The method comprises the following steps:

(1) urea adduction: adducting a mixture including a raw material, urea and a lower alcohol aqueous solution at a temperature of 45 to 65° C., wherein a ratio of the raw material to the urea is 1:1 to 4, a ratio of the urea and the lower alcohol is 1:3 to 6; and then crystallizing at 0-10° C. of crystallization temperature; and afterwards filtratiing to obtain a filtrate of unsaturated substances and a filter cake of urea-saturated substance adducts; and then removing solvent from the filtrate to obtain the target unsaturated components, and the filter cake is a urea adduct.

(2) releasing the urea adduct: adding a polar solvent to the urea adduct to form a solution, wherein the polar solvent is water, lower alcohol, or a mixture of water and lower alcohol in any proportion; then heating and stirring the solution for dissolution at a temperature of 50 to 90° C., and standing for layering to obtain a urea solution; and then washing the upper layer of the urea solution with water to obtain a component adducted by urea;

(3) urea crystallization: adding an organic solvent to the lower layer of the urea solution, wherein the organic solvent is lower alcohol, n-hexane, acetone, aether, ethyl acetate, or a mixture thereof in any proportion; and then stirring and mixing, cooling for crystallization slowly; and afterwards filtering, and drying to obtain urea crystals for urea reuse.

Preferably, the target unsaturated components of step (1) comprise VE, unsaturated fatty acids, or their methyl esters or ethyl esters, squalene, and other liposoluble substances containing unsaturated double bonds; the saturated substances are other components with higher saturation relative to the unsaturated substances.

Preferably, the polar solvent of step (2) comprises water, lower alcohol or a mixed solution thereof, and the volume of adding the polar solvent of step (2) is 0.5 to 10 times as much as the mass of the urea adduct. The lower alcohol is a C1 to C4 saturated aliphatic alcohol.

Preferably, the polar or non-polar solvent of step (3) comprises but is not limited to lower alcohol, n-hexane, acetone, ethyl ether, ethyl acetate, or a mixture thereof in any proportion. The lower alcohol is a C1 to C4 saturated aliphatic alcohol. More preferably, the volume of adding the organic solvent of step (3) is 0.3 to 10 times as much as the volume of an original solution.

Preferably, the crystallization temperature of step (3) is −5 to 0° C., more preferably, the crystallization time of step (3) is 1 to 24 hrs.

Preferably, the recovery rate of step (4) is more than 80%.

The process route of the present invention is to realize a separation between different saturation components and to obtain unsaturated components and urea-more saturated component adducts respectively by adducting samples to be separated and urea and then crystallizing and filtering. And then the urea adduct is dissolved in a polar solvent to layer in order to completely release adducted components. Finally, adding a certain amount of solvents to the urea solution adjusts a polarity of system, to realize recycling and reusing of urea after cooling for crystallization.

The step (2) is a urea adduction step. A raw material, urea and a lower alcohol aqueous solution is adducted at a temperature of 45-65° C., wherein a proportion of raw material to urea is 1:1 to 4, a proportion of urea to alcohol is 1:3 to 6; and then crystallized at a temperature of 0-10° C.; and afterwards filtered to obtain a filtrate of unsaturated substances and a filter cake of urea-saturated substance adducts; and then remove solvent from the filtrate to obtain target unsaturated components, and the filter cake is a urea adduct. Wherein, the preferred crystallization time is not less than 2 hours. Here, both of the different sample compositions and different target products need to be adjusted correspondingly within a ratio range in order to obtain desired purity and a recovery rate of target unsaturated components. In addition, the adduction temperature, the crystallization temperature and the crystallization time also have a significant impact on the purity and the recovery rate of the product.

The urea recycling and reusing of steps (2) to (4) comprises release of the adducted substances and crystallization of urea. In particular, a urea adduct is dissolved in a certain amount of polar solvents, so as to make encapsulated molecules released from urea molecules, and consequently achieve two-phase separation from a urea solution. The recovery rate of urea of the present invention is more than 80% and achieves recycling of urea by adding a certain amount of solvent to the urea solution and changing solubility of urea through adjusting the polarity of the system and promoting crystallization of urea at low temperature conditions.

DETAILED DESCRIPTION AND PREFERRED EMBODIMENTS THEREOF

Hereafter, the present invention will be described specifically with reference to the examples. The examples are given only for illustration of the technical solution of the present invention and should not be construed to limit the present invention.

Example 1

A methyl esterification product from soybean deodorized distillate is added into urea and 95% methanol aqueous solution in a certain proportion to form a mixture, wherein methyl esterification product:urea:methanol=1:2:10 (m:m:v). The mixture is stirred at a temperature of 50° C. until it becomes a clear solution, and then is cooled to 6° C. slowly, stood for crystallization; and afterwards recycle solvent from a filtrate and rectify to obtain a product with the content of more than 70% squalene.

Releasing adducted substances: a filter cake (i.e. urea adduct) obtained after filtration is added to water with 0.5 times mass as much as the mass of the filter cake, and stirred at a temperature of 90° C. until it becomes a clear solution, and then stood for layering.

Recycling urea: 0.3 times volume of acetone as much as the volume of a lower layer urea solution is added to the lower layer urea solution, and mixed uniformly, slowly cooled to a temperature of −5° C., stood for crystallization for 1 hour, then filtrated to a crystal and then dried to obtain urea crystals recycled, and the recovery rate of the urea is more than 85%.

Reusing of urea: the recycled urea is reused for the urea adduct process of the methyl esterification product from soybean deodorized distillate. The testing result shows no significant effect on the purity of squalene in the obtained products.

Example 2

A soybean oil is saponified and acidified to obtain a free type fatty acid, and then the free type fatty acid, urea and 95% ethanol aqueous solution in a ratio of 1:1:3 (m:m:v) are mixed uniformly at a temperature of 65° C., and afterwards cooled to a temperature of 10° C. for crystallization, filtered under vacuum to obtain a filtrate. The filtrate is vacuum-evaporated, washed with water to obtain the content of 87.8% of linoleic acid product.

Releasing the adducted fatty acid: a filter cake (i.e. a urea-fatty acid adduct) obtained by filtering a filtrate is added to a 70% ethanol aqueous solution with 3 times mass as much as the mass of the filter cake, stirred for 30 minutes at a temperature 50° C., then stood for layering. The upper oil layer is washed with water to obtain saturated and monounsaturated fatty acids containing palmitic acid, stearic acid, oleic acid and a small amount of linoleic acids.

Recycling urea: 0.5 times volume of n-hexane as much as the volume of the lower layer solution is added to the lower solution, and then mixed uniformly, cooled to 5° C. of temperature, stood for crystallization for 16 hours, and afterwards filtered to produce crystals. The crystals are dried to obtain urea crystals recycled, and the recovery rate of the urea is more than 85%.

Example 3

The urea obtained by recycling of Example 2 will be conducted for a urea adduct test according the above mentioned conditions, and conducted for many repeated recycling and application. The content of linoleic acid for each time is shown in the following Table. It can be seen from the table that the urea recycled by this method is recycled completely and does not affect the reuse effects.

| | Times of Application | | | | | | | | | |
|---|---|---|---|---|---|---|---|---|---|---|
| | 1 | 2 | 3 | 4 | 5 | 6 | 7 | 8 | 9 | 10 |
| Linoleic acid content (%) | 87.8 | 87.1 | 88.5 | 86.7 | 86.2 | 88.2 | 87.9 | 87.7 | 87.1 | 88.0 |

Example 4

Ethyl ester type fish oil, urea and 95% methanol aqueous solution in a ratio of 1:4:12 (m:m:v) are mixed uniformly at a temperature of 45° C., then cooled to a temperature of 0° C. for crystallization, and then filtered under vacuum to obtain a filtrate. The filtrate is vacuum-evaporated to obtain a fish oil product with a total content of 90% DHA, EPA.

Releasing the adducted fatty acid: a filter cake (i.e. a urea adduct) obtained by filtering a filtrate is added to methanol with 10 times mass as much as the mass of the filter cake, and stirred at a temperature of 70° C. until dissolved, then stood for layering. The upper oil layer is washed with water to obtain higher saturated fatty acid ethyl esters.

Recycling the urea: 5 times volumes of ethyl acetate as much as the volume of the lower layer urea solution is added to the lower layer urea solution, and then cooled to a temperature of 20° C. slowly, stood for crystallization for 24 hours, then filtered to obtain urea crystals recycled, and the recovery rate of the urea is more than 90%.

Recycling of the recovered urea: the recovered urea is used to continue to perform a adduction separation for ethyl ester type fish oil. The total content of DHA, EPA obtained is not changed obviously relative to initial uses, and up to 90%.

Example 5

Urea adduction: A sunflower seed oil is saponified and acidified to obtain a free type sunflower seed oil fatty acid, and then 100 g of the free sunflower seed oil type fatty acid, 400 g of urea and 1200 ml of 95% ethanol aqueous solution are mixed uniformly and stirring at a temperature of 60° C., and afterwards cooled to a temperature of 10° C. for crystallization, stood for crystallization for 6 hours, and then filtered under vacuum for separating filtrates and solid crystals. The filtrate is under vacuum-evaporated to obtain the content of morer than 80% of α-linolenic acid product.

The solid crystals (i.e. solid adduct) are dissolved and stirred to 4 times mass of water as much as the mass of the solid adduct at a temperature of 60° C., stood for layering. The upper oil layer is washed with water to obtain fatty acids with less than 3 of unsaturation comprising palmitic acid, stearic acid, oleic acid, linoleic acid and a small amount of linolenic acid.

Two times volumes of methyl alcohol as much as the volume of the lower layer solution is added to the lower layer solution, and then cooled to a temperature of 4° C. slowly, stood for crystallization for 8 hours, and afterwards filtered to obtain crystals. The crystals are dried to obtain urea crystals recycled, and the recovery rate of the urea is more than 90%.

Example 6

Palm oil is processed with urea adduct after methyl esterification. Palm oil methyl-esterified, urea and 95% methanol aqueous solution in a ratio of 1:2:12 (m:m:v) are mixed uniformly and stirred at a temperature of 60° C. until it become a clear solution, and then cooled to 4° C. slowly for crystallization. After filtration, a filtrate is concentrated, crystallizated or distilled to prepare VE, and the content of VE component can reach more than 80%.

Two times mass of 40% methanol solution as much as the mass of the filter cake is added to a filter cake (i.e. urea adduct) obtained from filtration, stirred for 45 minutes at a temperature of 50° C. until it become a clear solution, and stood for layering. The upper layer is liposoluble substances adducted by urea, and the lower layer is ethanol aqueous solution of urea.

Ten times volume of ether as much as the volume of the lower layer solution (i.e. ethanol aqueous solution of urea)

is added to the lower layer solution and mixed uniformly, and then cooled to 0° C. slowly and stood for crystallization for 12 hours, and afterwards filtered and dried to recycle urea crystals. The recovery rate is 80% to be reused for the urea adduct process.

It can be seen from the Examples 1 to 6 that the recovery rate of urea is more than 80% by using the method of the present invention.

Although the present invention has been described in connection with the above embodiments, it should be understood that the present invention is not limited to such preferred embodiments and procedures set forth above. The embodiments and procedures were chosen and described in order to best explain the principles of the invention and its practical application, to thereby enable others skilled in the art to best utilize the invention. It will be apparent to those skilled in the art that various substitution, modifications and changes may be thereto without departing from the scope and spirit of the invention. Therefore, the intention is intended to cover all alternative constructions and equivalents falling within the spirit and scope of the invention as defined only by the appended claims and equivalents thereto.

The invention claimed is:

1. A method of recycling urea in a process of purifying unsaturated substances through a urea adduction method, comprising the following steps:
   (1) urea adduction: adducting an aqueous solution including a raw material, urea and a lower alcohol aqueous solution at a temperature of 45-65° C., wherein a ratio of the raw material to the urea is 1:1-4, a ratio of the urea and the lower alcohol is 1:3-6, and then crystallizing at 0-10° C. of crystallization temperature; and afterwards filtering to obtain a filtrate of unsaturated substances and a filter cake of urea-saturated substance adducts; and then removing solvent from the filtrate to obtain one or more target unsaturated components, and the filter cake is a urea adduct;
   (2) releasing the urea adduct: adding a volume of a polar solvent to the urea adduct to form a solution, wherein the polar solvent is lower alcohol, or a mixture of water and lower alcohol in any proportion, then heating and stirring the solution for dissolution at a temperature of 50 to 90° C., and standing for layering to obtain a urea solution having an upper layer and a lower layer, and then washing the upper layer of the urea solution with water to obtain a component adducted by urea; and
   (3) urea crystallization: adding a volume of an organic solvent to the lower layer of the urea solution, wherein the organic solvent is lower alcohol, n-hexane, acetone, ether, ethyl acetate, or a mixture thereof in any proportion; and then stirring and mixing, cooling for crystallization slowly to crystallize at a crystallization temperature, and afterwards filtering, and drying to obtain urea crystals for urea reuse.

2. The method according to claim 1, wherein the one or more target unsaturated components of step (1) comprise vitamin E, unsaturated fatty acids, or their methyl esters or ethyl esters, squalene, and other liposoluble substances containing unsaturated double bonds and wherein the saturated substances are other components with higher saturation relative to the unsaturated substances.

3. The method according to claim 1, wherein the crystallization time of step (1) is not less than 2 hours.

4. The method according to claim 1, wherein the volume of adding the polar solvent of step (2) is 0.5 to 10 times as much as the mass of the urea adduct.

5. The method according to claim 1, wherein the volume of adding the organic solvent of step (3) is 0.3 to 10 times as much as the volume of an original solution.

6. The method according to claim 1, wherein the crystallization temperature of step (3) is −5 to 20° C.

7. The method according to claim 6, wherein a time for cooling for crystallizing of step (3) is 1 to 24 hrs.

8. The method according to claim 1, wherein a recovery rate of urea after crystallization of step (3) is more than 80%.

9. The method according to claim 1, wherein the lower alcohol is a C1 to C4 saturated aliphatic alcohol.

10. The method according to claim 1, wherein the lower alcohol of step 1 is an aqueous methanol solution.

11. The method according to claim 1, wherein the lower alcohol of step 1 is an aqueous ethanol solution.

12. The method according to claim 1, wherein the organic solvent in step (3) is selected from the group consisting of lower alcohol, n-hexane, acetone, ether, or a mixture thereof.

13. The method according to claim 1, wherein the organic solvent in step (3) is a lower alcohol.

14. The method according to claim 1, wherein the organic solvent in step (3) is n-hexane.

15. The method according to claim 1, wherein the organic solvent in step (3) is acetone.

16. The method according to claim 1, wherein the organic solvent in step (3) is ether.

* * * * *